(12) United States Patent
Demoulin et al.

(10) Patent No.: US 10,645,959 B2
(45) Date of Patent: May 12, 2020

(54) METHOD AND DEVICE FOR TREATING AND MONITORING THE QUALITY OF OBJECTS COMPRISING METAL MATERIALS

(71) Applicant: Red Bull GmbH, Fuschl am See (AT)

(72) Inventors: Gunnar Demoulin, Salzburg (AT); Christian Rinderer, Fuschl am See (AT); Roland Concin, Fuschl am See (AT)

(73) Assignee: Red Bull GmbH, Fuschl am See (AT)

( * ) Notice: Subject to any disclaimer, the term of this patent is extended or adjusted under 35 U.S.C. 154(b) by 414 days.

(21) Appl. No.: 15/268,671

(22) Filed: Sep. 19, 2016

(65) Prior Publication Data

US 2018/0077953 A1    Mar. 22, 2018

(51) Int. Cl.
*B65B 57/18*    (2006.01)
*A23L 3/04*    (2006.01)
(Continued)

(52) U.S. Cl.
CPC .................. *A23L 3/04* (2013.01); *A23L 2/46* (2013.01); *A23L 3/003* (2013.01); *A23L 3/02* (2013.01); *B65B 25/001* (2013.01); *B65B 55/06* (2013.01); *B65B 55/10* (2013.01); *B65B 57/18* (2013.01); *C23G 3/02* (2013.01); *C23G 3/027* (2013.01); *G01N 21/25* (2013.01); *G01N 21/909* (2013.01);
(Continued)

(58) Field of Classification Search
CPC ....... B65B 25/001; B65B 55/02; B65B 57/00; B65B 55/06; B65B 55/10; B65B 57/18; A23L 2/46; A23L 3/001; A23L 3/003; A23L 3/02–3/14; G01N 21/25; G01N 2021/8411–2021/8416; G01N 21/90–21/909; G01N 33/20; G01N 2033/0081; G01N 2201/062; C23G 3/02; C23G 3/027; A23V 2002/00
USPC ................ 426/231–232, 407–408, 521–522; 356/240.1, 237.2; 99/337, 341–344
See application file for complete search history.

(56) References Cited

U.S. PATENT DOCUMENTS 2,342,199 A * 2/1944 Hurtt ........................ B21B 27/10
                                                           72/199
3,445,179 A * 5/1969 Jansen .................... A23L 3/045
                                                           122/379
(Continued)

FOREIGN PATENT DOCUMENTS

CN        101588823 A     11/2009
CN        105658083 A      6/2016
(Continued)

OTHER PUBLICATIONS

Aluminum Association NPL, Guidelines for Minimizing Water Staining of Aluminum, May 2009, p. 1-10.*

*Primary Examiner* — Drew E Becker
(74) *Attorney, Agent, or Firm* — Collard & Roe, P.C.

(57) ABSTRACT

A method and a device for treating and monitoring objects incorporating a metal material. The objects are treated with a treatment fluid in one or more treatment zone(s) and the treatment fluid is then removed from and/or dried on the objects. To provide constant quality monitoring, at least one portion of at least one object respectively is optically detected and calorimetrically evaluated. In this manner, discoloration of metal materials caused by the treatment can be promptly detected.

20 Claims, 4 Drawing Sheets

(51) Int. Cl.
  *A23L 3/00* (2006.01)
  *C23G 3/02* (2006.01)
  *G01N 21/25* (2006.01)
  *G01N 21/90* (2006.01)
  *A23L 3/02* (2006.01)
  *A23L 2/46* (2006.01)
  *B65B 25/00* (2006.01)
  *B65B 55/06* (2006.01)
  *B65B 55/10* (2006.01)
  *G01N 33/20* (2019.01)
  *G01N 21/84* (2006.01)

(52) U.S. Cl.
  CPC ...... *G01N 33/20* (2013.01); *G01N 2021/8411* (2013.01); *G01N 2201/062* (2013.01)

(56) References Cited

U.S. PATENT DOCUMENTS

| | | | | |
|---|---|---|---|---|
| 3,749,923 A * | 7/1973 | Husome | ................ | B07C 5/342 209/528 |
| 3,769,932 A * | 11/1973 | Romito | ................ | G01K 1/14 116/207 |
| 4,303,546 A * | 12/1981 | Waegerle | ................ | C02F 5/10 252/180 |
| 4,696,580 A * | 9/1987 | Kameda | ................ | G01K 3/04 374/162 |
| 4,705,703 A * | 11/1987 | Meier | ................ | C23F 11/08 106/14.12 |
| 4,735,508 A * | 4/1988 | Bellio | ................ | G01B 11/255 209/524 |
| 4,798,675 A * | 1/1989 | Lipinski | ................ | C02F 5/14 210/699 |
| 4,846,898 A * | 7/1989 | Natalie | ................ | C09D 5/00 428/469 |
| 5,245,399 A * | 9/1993 | Wertz | ................ | B07C 5/342 250/226 |
| 5,374,988 A * | 12/1994 | Wertz | ................ | B07C 5/342 356/237.2 |
| 5,386,293 A * | 1/1995 | Barnard | ................ | G01N 21/909 348/125 |
| 5,699,152 A * | 12/1997 | Fedor | ................ | G01N 21/909 356/240.1 |
| 5,707,553 A * | 1/1998 | Sawyer | ................ | C23F 11/141 252/390 |
| 5,804,237 A * | 9/1998 | Diamond | ................ | A23L 3/02 426/131 |
| 6,122,048 A * | 9/2000 | Cochran | ................ | G01N 21/8806 250/223 B |
| 6,151,064 A * | 11/2000 | Connolly | ................ | G01J 3/50 348/93 |
| 6,233,966 B1 | 5/2001 | Delpuech et al. | | |
| 6,519,356 B1 * | 2/2003 | Hooker | ................ | G01N 21/9036 209/524 |
| 6,654,116 B1 * | 11/2003 | Kwirandt | ................ | G01N 21/909 209/524 |
| 8,096,138 B2 * | 1/2012 | Dhruv | ................ | A23L 3/36 426/407 |
| 8,156,714 B2 | 4/2012 | Münzer | | |
| 9,873,535 B2 * | 1/2018 | Liu | ................ | A01N 37/04 |
| 2002/0011280 A1 * | 1/2002 | Nitowski | ................ | B05D 1/185 148/253 |
| 2002/0073652 A1 | 6/2002 | Wiedemann | | |
| 2003/0024554 A1 | 2/2003 | Schultz et al. | | |
| 2008/0291439 A1 * | 11/2008 | Sones | ................ | G01N 21/8851 356/240.1 |
| 2009/0130268 A1 * | 5/2009 | Euler | ................ | A61L 2/22 426/232 |
| 2009/0316145 A1 * | 12/2009 | Widera | ................ | G01B 21/042 356/240.1 |
| 2011/0217204 A1 * | 9/2011 | Franciskovich | ................ | A01N 37/16 422/29 |
| 2012/0282136 A1 * | 11/2012 | Richardson | ................ | C23F 11/18 422/38 |
| 2014/0098365 A1 * | 4/2014 | Kurosawa | ................ | G01N 21/909 356/240.1 |
| 2015/0211129 A1 | 7/2015 | Juricic et al. | | |
| 2018/0195974 A1 * | 7/2018 | Kress | ................ | G01N 21/8806 |

FOREIGN PATENT DOCUMENTS

| | | |
|---|---|---|
| DE | 10 2012 015 579 A1 | 2/2014 |
| EP | 0 965 021 B1 | 7/2002 |
| EP | 1 862 307 A2 | 12/2007 |
| EP | 2 899 535 A1 | 7/2015 |
| JP | 2005-181072 A | 7/2005 |
| WO | 94-19968 A1 | 9/1994 |
| WO | 2006/101944 A2 | 9/2006 |
| WO | 2015/065489 A1 | 5/2015 |

\* cited by examiner

METHOD AND DEVICE FOR TREATING AND MONITORING THE QUALITY OF OBJECTS COMPRISING METAL MATERIALS

BACKGROUND OF THE INVENTION

1. Field of the Invention

The invention relates to a method and a device for treating and monitoring the quality of objects comprising a metal material.

2. The Prior Art

Metal materials are often used in objects or goods due to their properties and the corresponding objects or goods may be made entirely from metal materials or from a combination of metal and non-metal materials. Containers comprising or made from a metal material are an example of this.

Due to the basic strength and dimensional stability of metal materials, such as aluminum, such containers may be designed with thin walls. Amongst other things, containers made from metal materials are also suitable for preserving sensitive contents, such as foodstuffs. In this respect, another advantage is their excellent gas barrier properties or very low permeability to gases, as is the case with aluminum or aluminum materials, for example. The foodstuffs can be prevented from spoiling over time, thereby resulting in a long shelf life for foodstuffs packaged in such containers.

Items or objects comprising a metal material are often treated with a treatment or process fluid. Amongst other things, this might be necessary during the actual production of the objects, such as for cleaning or tempering purposes, in particular for cooling the objects after shaping, etc. Alternatively, such a treatment with a treatment fluid might be carried out for other purposes. An example of this is a treatment of containers incorporating metal material with a heated process fluid for the purpose of pasteurizing a foodstuff contained in the containers. A treatment of an object comprising a metal material does not comprise a coating of the metal material, such as a varnishing or lacquering or the like.

When treating an object made from an uncoated metal material, a change to the metal material may occur in principle during the course of a lengthy or continuous treatment with treatment fluid over time. Such changes might be of a chemical nature, for example due to surface oxidation processes. Chemical-physical changes may likewise be induced at the surface structure due to such treatments with fluids, for example in layers of the metal materials close to the surface. Such superficial changes in a metal material caused by a treatment fluid may occur in particular in the case of treatment methods in which one and the same treatment fluid is used repeatedly for treating the objects. This is primarily because a repeated treatment of objects with the same treatment fluid can lead to changes in the chemical composition of the treatment fluid. A treatment fluid chemically altered in this manner can in turn lead to changes close to the surface of a metal material during the course of a treatment, at most leading to discoloration of the metal material.

In the case of metal materials, a change in composition or a change in the surface structure of a metal material is often accompanied by a visually perceptible or evident change to the color of the material. This often depends on the type of change to a metal material, which in turn is often dependent on the properties and composition of the treatment fluid. In the case of treating an object containing an uncoated aluminum material with an aqueous treatment fluid, a so-called wet storage stain can occur, for example. Such treatments with a heated, aqueous treatment fluid are often carried out for the purpose of pasteurizing foodstuffs packaged in aluminum containers.

In principle, such changes do not always impair the function of the object or article comprising the metal material, being merely changes close to the surface. However, perceptible discoloration of objects or products is often perceived by consumers as meaning a reduction in quality or even as a possible product fault. Such objects are often no longer viewed as acceptable by consumers and a discolored object or product may then no longer be commercially usable, for example, or may be so but under limited conditions.

This being the case, especially from a commercial point of view, it is in particular problematic if such changes, for example discoloration, during a treatment go unnoticed or are not noticed until some time after they actually occurred. In modern mass production, high batch quantities are often produced in a continuous process. If a change during a process goes undetected or is detected late on, it may be that a whole batch of objects is substandard. For this reason, there is a need for means for monitoring production processes involving a treatment of objects incorporating metal materials with a fluid, in, particular an aqueous treatment fluid.

SUMMARY OF THE INVENTION

The objective of this invention was to meet this need and propose a method and a device enabling changes to objects incorporating a metal material to be detected as easily as possible during the course of a treatment with treatment fluid.

This objective is achieved by a method and a device as defined in the claims.

The inventive method for treating and controlling or monitoring the quality of objects comprising a metal material comprises at least one method step for treating the objects incorporating a metal material with a treatment fluid, in particular with an aqueous treatment fluid, in a treatment zone or in several treatment zones. After the treatment, the treatment fluid is either actively removed from the treated objects or the treatment fluid is passively dried from the treated objects.

To provide constant or continuous monitoring after treating the objects, at least one portion of at least one object comprising a metal material having been treated with treatment fluid is optically detected by means of a color-detecting detection device.

The optically detected data and/or color data of the at least one portion is colonmetrically evaluated in order to detect discoloration by means of an evaluation device by determining a color value or several color values. This evaluation may be run on the basis of a color model.

The expression metal material should be understood in particular as meaning metals and metal alloys. The treatment with the treatment fluid does not comprise a coating of the metal material. The metal material therefore is uncoated, and also is not coated in course of the treatment. The objects comprising a metal material may be metal containers or closing caps for glass containers or plastic containers, for example screw-caps made of metal material, or the like.

The treatment fluid may specifically be reused to treat the objects, in other words for repeatedly treating the objects in the treatment zone(s). To this end, the treatment fluid may be circulated in a circuit and repeatedly delivered to the treatment zone(s), for example.

Due to the specified features, a method is proposed which above all enables the detection of imperfections as early as possible and a calorimetric evaluation of discoloration of metal materials during ongoing operation of the treatment of objects with treatment fluid. This results in a highly efficient treatment of the objects with treatment fluid. In particular, the risk of faulty or defective treatment for large batch quantities of objects can be minimized as far as possible. If a significant discoloration and/or color change on a metal material induced by treatment is found by detection and colorimetric evaluation, counter-actions can be taken in order to prevent and/or avoid further defective treatment of large quantities of objects with the treatment fluid and the associated discoloration of the metal material. This enables high losses, in particular commercial losses, due to objects or goods that can only be sold under certain circumstances to be effectively prevented.

There is a particularly high risk of discoloration and/or changes in metal materials in the case of treatments with aqueous fluids. Many metal materials exhibit changes, in particular chemical changes, in an aqueous environment. These include oxidation, salt formation or surface dissolution, for example. In particular, heated aqueous treatment fluids and/or condensation of the treatment fluid on metal materials can lead to changes and/or discoloration. If using aqueous treatment fluids, it is therefore of particular advantage to be able to detect and run a numerical evaluation of discoloration as soon as possible.

However, generally speaking, aqueous treatment fluids can be of advantage from many points of view and are therefore often used for treating objects incorporating a metal material. IFor example, cleaning or surface or tempering treatments of objects incorporating metal can be run efficiently with aqueous treatment fluids. This is especially the case because the properties of aqueous fluids can be very efficiently and specifically adjusted by the addition of chemicals. An aqueous treatment fluid containing specific appropriate chemicals can be used to selectively treat a specific metal material of the respective objects. Furthermore, aqueous treatment fluids can be tempered in a relatively broad temperature range and aqueous treatment fluids are readily available.

The treatment fluid on the objects can be removed or dried both actively and passively in principle. For example, the treatment fluid can be removed by passive draining and/or passive evaporation or steaming off of the treatment fluid from the treated objects. Alternatively, an active and/or assisted removal of the treatment fluid may be provided. For example, in the case of active removal of the treatment fluid, the objects can be conveyed to another zone and/or treatment zone with a drying climate and/or actively dried in an air flow, preferably a hot air flow.

In principle, the system may be such that at least a part quantity is constantly or continuously monitored and/or at least one of the objects treated with treatment fluid is constantly monitored by optically detecting at least one portion. In principle, it is possible on this basis to optically detect in each case at least one of the objects treated with treatment fluid at set time intervals or after treating a set number of objects with treatment fluid. Detection on the basis of random samples would also be conceivable, in which case optical detection of at least one of the objects treated with treatment fluid may also take place at irregular intervals. Optical detection on the basis of random sampling of at least one portion of at least one object respectively may be carried out manually or by hand by an operator. However, it would also be possible for the at least one portion of all the treated objects to be optically detected. The latter operating mode represents a relatively complex but particularly reliable approach.

In principle, it would also be conceivable for several portions or even all portions of an object treated with treatment fluid to be detected for monitoring purposes. In most cases, however, optical detection can be limited to one portion of an object, in particular a portion where a change caused by treatment with a treatment fluid is particularly likely.

The color-detecting detection device may in principle be based on any type of detection device by means of which light and/or colors can be reliably detected, for example by color measuring devices operating on the basis of spectral resolution or spectral photometry. In principle, color sensors may also be used. In this case however, these should be used on a limited basis in terms of detecting a restricted spectral range. Preferred embodiments of the color-detecting detection device will be explained in more detail below.

A quantitative calorimetric evaluation can be operated on the basis of a color model. Examples of color models include the CMYK color model or the RGB color space or the L*a*b* color space. In this case, the detected color and/or the detected tone is broken down or classified and described on the basis of color values in terms of spectral composition and color properties, such as brightness or saturation. On the basis of such color models, a color and/or color stimulus can therefore be described by numerical color values. In particular, these color values may define a color and/or color stimulus of a so-called color locus in a color space which represents and/or identifies the optically detected color and/or color stimulus in the co-ordinate system of the respective underlying color space. On the basis of one or more such color values, an evaluation of the optically detected data and/or color data can be run and any discoloration can be quantitatively detected on an automated basis and numerically described.

The advantage of this is that a colorimetric evaluation and/or a numerically determined color value or several color values can be used to assess a color change of the at least one detected portion of an object without the need for a continuous, subjective visual assessment of the object by a human being. Color values automatically determined by the evaluation device on the basis of colorimetry can then also be further numerically processed and can be visually displayed, for example, or computed to provide automated triggering of an action.

It is also possible for numerical color values to be stored for future use with little memory space. On the basis of stored data sets of color values, statistical evaluations can be easily run and displayed, for example. The advantage of this, amongst other things, is that the stored color data sets can be used for subsequent analysis, for example to establish and/or verify a time correlation between detected discoloration of the objects and specific events or environmental influences and such like.

Based on another embodiment of the method, the objects can be conveyed by means of a conveyor in a transport direction through one or more consecutive treatment zone(s) and having passed through the treatment zone or having passed through the last one of the consecutive treatment zones in the transport direction, the at least one portion of the respective at least one object to be detected or all of the objects treated with treatment fluid is or are optically detected.

This represents a particularly efficient, largely automatable and continuous operating method for treating the objects with treatment fluid.

Furthermore, it may be of practical advantage if the at least one object to be detected and/or monitored is conveyed through a control zone incorporating the color-detecting detection device.

In this manner, optical detection of the at least one portion of at least one of the objects treated with treatment fluid can be automated as far as possible to enable continuous and hence efficient operation. This being the case, a control zone comprises the optical detection device disposed or installed in a region down-stream of one of the or the treatment zone(s) in such a way that a part quantity of the objects treated with treatment fluid or all the treated objects can be optically detected, for example.

In, principle, objects containing an aluminum material can be treated with aqueous treatment fluid and at least one portion of the at least one object incorporating aluminum material can be optically detected in each case.

In this manner, discoloration which often occurs during the treatment of objects comprising aluminum material with aqueous treatment fluid, namely so-called wet storage stain or water staining, can be optically detected and/or colorimetrically evaluated. By aluminum material is meant in particular aluminum and aluminum alloys.

Based on one variant of the method, a respective external face of the objects can be treated with a tempered treatment fluid in at least one treatment zone, for example.

Treatments with a tempered treatment fluid are particularly suitable as a means of heating or cooling objects comprising a metal material in a specific way. In this manner, the result of the treatment can be controlled and/or influenced by the respective temperature of the treatment fluid, for example in order to cool the objects by means of the treatment fluid in a specific way after a preceding method step.

Furthermore, the objects can be treated in at least one treatment zone with a treatment fluid having a temperature of between 45° C. and 130° C. In particular, the objects can be treated with a treatment fluid having a temperature of between 50° C. and 100° C., in particular between 60° C. and 90° C.

Generally speaking, treatment operations for objects based on a treatment with a heated treatment fluid can be run more efficiently. This might be the case with a cleaning process for the objects, for example.

However, a treatment with a tempered treatment fluid might be provided for other purposes.

For example, the objects might be containers and the containers may be filled with contents, in particular with a foodstuff, and closed prior to the treatment with treatment fluid.

In this case, tempering of the external face of the objects or containers might be carried out for the purpose of indirectly tempering the contents or foodstuff contained in the container. The advantage of this is that the treatment fluid does not come into direct contact with the contents or foodstuff. Potential negative effects of the treatment fluid on the contents can be ruled out in this manner but the contents of the containers can still be tempered. For example, a foodstuff can be heated in a specific way for treatment purposes or can be selectively cooled for conservation purposes.

In particular, the containers can be filled with a foodstuff and closed and the foodstuff can be pasteurized in the at least one treatment zone.

The shelf life of a foodstuff can be significantly increased as a result of this operating method.

In one operating mode, the treatment fluid can advantageously be removed from the at least one object respectively, prior to optical detection of the at least one portion.

As a result, parasitic effects induced by the treatment fluid can be prevented, such as the effects of reflection or the effect of scattered light, or coloration of the treatment fluid during optical detection of the at least one portion of the at least one object. In particular, distortion and/or a false result of the colorimetric evaluation caused by the treatment fluid can be prevented. In this case, the treatment fluid can be removed by passive draining and/or evaporation of the treatment fluid from the object, for example. The treatment fluid is preferably actively removed from the at least one object or with assistance, for example using an air flow, in particular a hot air flow, or by generating a negative pressure, for example.

Based on a preferred variant of the method, a detection area of the color-detecting detection device in a control zone is partitioned off or screened off from ambient light at least as far as possible, and the at least one portion respectively of the at least one object to be optically detected can be illuminated with white light by means of an illuminating device, in particular by means of an LED-illuminating device.

This results in a method for monitoring and/or for optical detection which can be operated at least largely independently of the effect of a respective ambient light. In particular in this manner, this enables the most objective possible and above all reproducible detection of discoloration of the objects due to the treatment with treatment fluid. Providing illumination with white light and keeping conditions as constant as possible also enables the detection and evaluation accuracy to be further increased and the color value or color values can be determined with increased reliability. All in all, this also enables the accuracy, reliability and reproducibility of the method steps for monitoring and/or controlling the quality of the objects to be improved.

Furthermore, an illuminating brightness of the illuminating device for the at least one portion to be optically detected can be adapted to a speed at which the object to be optically detected is conveyed through the control zone.

In this manner, a sufficient illuminating brightness or light intensity of the illuminating device can be selected for a respective illumination time for the respective at least one portion that is dependent on the conveying speed or conveying frequency. In particular, in the case of a high conveying speed of the object to be optically detected, a high illuminating brightness or high light intensity can be selected due to the relatively short illumination time possible. In the case of a lower conveying speed through the control zone, a relatively lower illuminating brightness can be selected because longer illumination times are possible.

It is also expediently possible to run a method whereby a threshold value can be set for the colorimetrically determined color value(s) and the colorimetrically determined color value(s) is/are compared with a respectively associated threshold value.

As a result, a respectively associated threshold value can be set for each color value determined by the colorimetric and/or evaluation system. By comparing a color value with the respectively associated threshold value, the extent of discoloration can be efficiently detected and assessed and/or numerically analyzed by computing means.

If a set threshold value is then exceeded by a color value associated with this threshold value, one or more action(s) can be implemented.

Operating a method in this manner means that intervention can be initiated as swiftly as possible if discoloration is detected or found. An action can then in principle be manually initiated by operating personnel of the device. Naturally, an action or a number of actions may also be initiated on an automated basis and/or by a control system. To this end, a control device may be connected to the evaluation device by signal transmission, which control device is configured to implement actions and/or counter-actions and/or to control the actions with appropriate action control means based on signal transmission after the computer system detects that a set threshold value has been exceeded.

For example, one action might be to trigger an alarm.

As a result, a detected or highlighted discoloration can be indicated as rapidly and efficiently as possible. An operator can then respond appropriately to the alarm, for example.

It may also be of practical advantage if the action undertaken is a change to the chemical composition of the treatment fluid.

Such changes to the chemical composition may be made with a view to preventing changes to a metal material during the course of the treatment with treatment fluid, thereby preventing the associated discoloration of the metal material. Such an action can in principle be instigated manually by the operating personnel. However, another option is to instigate a change of the chemical composition of the treatment fluid by automated and/or controllable means. For this purpose, for example, automated controllable valves and intake means may be provided, enabling chemicals to be added to the treatment fluid from tanks.

For example, another action might be to adjust the pH value of the treatment fluid and/or add inhibitors, in particular phosphonates, to the treatment fluid and/or add water hardness regulators to the treatment fluid.

The specified actions have proved to be particularly suitable for counteracting changes to a metal material and hence the associated discoloration of the material.

In the situation where the treatment fluid is used repeatedly to treat the objects, the action might be partially or totally replacing the treatment fluid, in other words at least partially replacing it with fresh treatment fluid. This action is of particular advantage in the case of methods where the treatment fluid of the treatment zone(s) is repeatedly fed into the process circuit.

However, it may also be of advantage if the action is to vary a conveying speed of the objects through the treatment zone(s) or to halt conveying of the objects.

In this manner, above all, by reducing the treatment rate and/or reducing the quantity of objects treated per unit of time, the number of defective objects or objects with undesired discoloration of a metal material can be reduced.

Alternatively or in addition, it may be of advantage if the action is to vary an intake temperature of a treatment fluid fed into a treatment zone.

This has also provided to be a suitable action in terms of preventing discoloration of a metal material during the course of a treatment with treatment fluid. Defects caused by discoloration can be at least temporarily avoided until other actions can be implemented to prevent discoloration. After implementing such other actions, for example a change to the chemical composition, the treatment fluid can then be fed back in at the original temperature suitable for treating the objects. Objects that were treated with treatment fluid at the altered temperature required by the specified action can then be fed back to the treatment system again if necessary.

Based on another preferred embodiment, the at least one optically detected portion of the respective at least one object can be evaluated calorimetrically in the L*a*b* color space and/or L*a*b* color space and the L* color value and/or a* color value and/or b* color value can be calorimetrically determined and/or numerically determined.

Amongst other things, a color detection evaluation in the L*a*b* color space is of advantage because a color model can be used for the evaluation that is configured or defined so as to be independent of the device and perception-based. In particular, this color space is well adapted and optimized for human perception of colors and/or color stimuli. As a result, any discoloration of metal materials can also be evaluated as effectively as possible in terms of human sensitiveness to discoloration.

In particular, so-called water staining of aluminum materials can be optically detected by means of the method and calorimetrically evaluated. This wet storage stain often occurs when aluminum materials come into contact with aqueous treatment fluids and detection of this discoloration is of great importance in connection with such treatment processes. However, the discoloration of aluminum materials known as wet storage stain can be difficult to detect and evaluate. In this connection, the b* color value can be calculated calorimetrically. Surprisingly, the b* color value has proved to be particularly well suited to optical detection and calorimetric evaluation of so-called wet storage stains. In particular, the brownish to black discoloration caused by water staining results in an increase in the b* color value towards higher positive values that can be readily evaluated calorimetrically.

The method is preferably implemented in such a way that the at least one portion of the at least one object is respectively optically detected by means of an imaging and/or color imaging detection means, in particular a color camera.

Due to this type of optical detection of least one object treated with treatment fluid respectively, detection of the at least one portion can be further improved. This is especially the case because the detected portion can be resolved by imaging. This represents an improvement compared with detection devices which merely give a mean value for the detected portion based on color values calculated by colorimetry. Furthermore, in this manner, discoloration can also be documented by images and archived or stored, for example for the purpose of assessment or comparison subsequently with other instances of discoloration.

In connection with image detection, the optically detected image of the at least one portion may be broken down into part-images and each part-image separately colorimetrically evaluated.

In this manner, discoloration in the at least one detected portion can be analyzed in certain regions or image positions. This enables points or areas exhibiting maximum discoloration to be identified, for example. This can in turn be helpful in determining how to prevent discoloration at these points or in these areas.

Based on another variant of the method, a test object and/or reference object can be treated with treatment fluid together with the objects to be treated, and a portion of the test object incorporating metal material can be optically detected by means of the color-detecting detection device after the treatment.

This enables a method to be implemented whereby optical detection of one of the objects regularly treated with treatment fluid is no longer necessary. This may be of advantage, for example, if the regular objects are relatively large and/or bulky items, whereas a corresponding test object can be made relatively small. This means that a control zone used for optically detecting the test object can be of relatively small dimensions. Furthermore, a corresponding test object can be reused.

In the situation where the objects are containers, only a portion of the corresponding container that is particularly susceptible to discoloration can be simulated by a test object, for example. For example, in the case of a treatment of aluminum containers in the form of cans, the test object might be a closure tab or so-called stay-on tab of the aluminum containers or cans. Such treatments, in particular with a heated treatment fluid, are often implemented for the purpose of pasteurizing foodstuffs with which the containers are filled. These closure or opening tabs of aluminum cans have been found to be particularly susceptible to discoloration or water staining during the course of a treatment for pasteurization purposes.

A test object can be conveyed through the treatment zone(s) together with the objects to be treated.

Accordingly, the test object can be subjected to the same treatment conditions as the rest of the objects.

However, the objective of this invention is also achieved by a device for treating and controlling and/or monitoring the quality of objects incorporating a metal material, in particular an aluminum material.

In this respect, the device comprises a treatment zone or several treatment zones for treating the objects, which treatment zone(s) has/have an intake means for delivering a treatment fluid.

The key aspect is that a control zone is provided, in which control zone a color-detecting detection device for optically detecting at least one portion of at least one object incorporating a metal material, in particular an aluminum material, respectively treated with treatment fluid is provided as a means of constantly and/or continuously monitoring the objects.

The color-detecting detection device is connected to an evaluation device by signal transmission to enable data processing of the optically detected data and/or color data of the at least one portion. The evaluation device is configured to colorimetrically evaluate the supplied data on the basis of a color model by determining a color value or several color values.

Due to the specified features, a device is provided, by means of which defects can be promptly and rapidly detected by detecting and colorimetrically evaluating discoloration of metal materials, in particular uncoated metal materials, during continuous operation of the treatment of the objects with treatment fluid. Such a device enables a highly efficient treatment of the objects with treatment fluid. In particular, the risk of faulty or defective treatment of large batch quantities of objects can be minimized as far as possible. In particular, discoloration on the metal material caused by the treatment can be promptly detected and prevented at least as far as possible by initiating counteractions.

The intake means may be provided in the form of a pipeline, for example, for feeding the treatment fluid into the treatment zone(s). In addition, the intake means may also comprise elements for selectively directing and/or distributing the treatment fluid in the treatment zone(s). Examples of this would be nozzles or spraying and/or sprinkler devices.

The device may comprise guide elements, for example pipes, in order to feed the treatment fluid through a circuit. In this manner, the treatment fluid can be repeatedly fed to the treatment zone(s) during operation of the device.

The color-detecting detection device may be based on any type of detection device by means of which light and/or colors can be reliably detected, for example by color measuring devices operating on the basis of spectral resolution or spectral photometry. In principle, color sensors may also be used. In this case however, these should be used to on a limited basis in terms of detecting a restricted spectral range. Preferred embodiments of the color-detecting detection device will be explained in more detail below.

In principle, the color-detecting detection device may be disposed and/or oriented in the control zone in such a way that at least a part quantity and/or at least one of the objects treated with treatment fluid can be continuously and/or constantly monitored by optically detecting the at least one portion. In principle, it is possible on this basis for the color-detecting detection device to optically detect in each case at least one of the objects treated with treatment fluid at set time intervals or after treating a set number of objects with treatment fluid. However, it would also be possible for the detection device to be disposed in the control zone in such a way that the at least one portion of all the objects treated with treatment fluid can be optically detected. To this end, the detection device may be a detection means with a large optical detection range. Alternatively, the detection device may also comprise a plurality of detection means to enable a large monitoring range to be optically detected.

In principle, it would also be conceivable for the detection device to comprise a plurality of detectors for detecting several portions, or even all portions of an object treated with treatment fluid. In most cases, however, optical detection can be limited to one portion of an object, in particular a portion where a change caused by treatment with a treatment fluid is particularly likely.

In principle, the evaluation device may be disposed separately from the detection device. In principle, any type of data transmission means may be used to transmit the optically detected data to the evaluation device. A hard-wired or wireless signal connection can be provided between the detection device and the evaluation device. The evaluation device may be provided in the form of a software controllable computer unit, such as a PC or a tablet, for example. In principle, however, the evaluation device may be an integrated component of the detection device, for example color sensors with an integrated evaluation device based on a color model.

Based on another embodiment of the device, after the treatment zone(s) for treating the objects with treatment fluid, another zone is provided for removing or drying the treatment fluid on the objects.

As a result, the treated objects can then be freed of treatment fluid after the treatment. This avoids allowing the treatment fluid to act for a longer period on an uncoated metal material of the objects after the treatment in the treatment zone(s) for treating the objects with treatment fluid. This in turn counteracts any potential changes and/or discoloration of a metal material due to the treatment fluid.

The other zone and/or treatment zone for removing the treatment fluid may be a simple storage room, for example, to which the objects treated with treatment fluid can be moved and in which storage room the treatment fluid can be drained and/or steamed off the objects. Optionally, the other treatment zone may be a closed, airconditioned room, for example, with a drying climate having a low, relative humidity and optionally an increased air temperature. Furthermore, the other zone for removing the treatment fluid may be provided with means for actively removing the treatment fluid from the objects, such as a fan, in particular a hot air fan.

Based on another embodiment, the device may comprise a conveyor means for conveying the objects through the treatment zone or several consecutive treatment zones.

Due to such conveyor means, the device can be operated efficiently, on a largely automated and continuous basis and the objects can be treated with treatment fluid at fast cycle times.

Furthermore, the conveyor means or another conveyor device may be provided for respectively conveying the at least one object to be detected through the control zone.

Due to this feature, optical detection of the at least one portion of at least one of the objects treated with treatment fluid can be automated as far as possible and run efficiently in continuous operation. In this respect, it may be, for example, that a control zone comprising the optical detection device is disposed or installed in an area downstream of one of the treatment zone(s) so that a part quantity of the treated objects or alternatively all of the objects treated with treatment fluid can be optically detected.

In principle, the control zone may be disposed following the last treatment zone relative to a transport direction of the objects.

In this manner, it can be guaranteed that the at least one object to be optically detected passes through the full treatment cycle and is thus representative of the objects treated with treatment fluid for control purposes.

It may also be expedient to opt for a design of the device whereby, following the last treatment zone for treating the objects with treatment fluid, relative to a transport direction of the objects, an additional treatment zone is provided for removing treatment fluid respectively from the at least one object to be optically detected.

For example, there might be a device for wiping off treatment fluid, or a drying device such as a hot air fan or similar device. The additional zone for removing treatment fluid can therefore be disposed between the last treatment zone for treating the objects with treatment fluid and the control zone, by reference to the transport direction.

Providing such an additional zone and/or treatment zone means that the treatment fluid can be rapidly removed from the at least one object to be detected. As a result, parasitic effects induced by the treatment fluid can be prevented, such as the effects of reflection or the effect of scattered light, or coloration of the treatment fluid during optical detection of the at least one portion of the at least one object. In particular, distortion and/or a false result of the colorimetric evaluation caused by the treatment fluid can be prevented. In this case, the treatment fluid can be removed by passive draining and/or evaporation of the treatment fluid from the object, for example. Preferably, the additional zone for removing the treatment fluid from the at least one object is provided with means for actively removing the treatment fluid and/or means for assisting its removal. These might be means for generating a drying climate in the additional treatment zone, for example, such as dehumidifying and tempering means. Alternatively or in addition, other means may be provided, such as a fan, in particular a hot air fan, or means for generating a negative pressure.

Based on another embodiment of the device, the device may comprise a heating means for heating the treatment fluid and a cooling means for cooling the treatment fluid and at least a first treatment zone can be provided for heating the objects. Following the first treatment zone, relative to a transport direction of the objects, at least a second treatment zone for additionally heating the objects can be provided. Furthermore, following the second treatment zone, relative to the transport direction of the objects, at least a third treatment zone can be provided for cooling the objects.

Due to such an arrangement of treatment zones and the supply to the treatment zones of treatment fluid at different temperatures, the objects can be tempered in a specific way, in particular heated in a specific way and cooled again in a specific way. In this manner, for example, foodstuffs with which the objects in the form of containers are filled can be conveyed through a gentle pasteurization process tempered in a specific way. One or more heating and cooling means may be provided, based in principle on any type of means for heating and/or cooling a treatment fluid, such as heating or cooling medium circulating through heat exchangers which can be supplied by heating and/or cooling devices. Steam heaters and/or cooling towers may be used, for example, or alternatively heat pumps.

Based on another embodiment of the device, the control zone comprises means for partitioning off or screening off the control zone from ambient light and an illuminating device, in particular an LED-illuminating device, is provided for illuminating the at least one portion respectively of the at least one object with white light.

As a result of these features, the at least one portion can be optically detected at least as independently as possible of the effect of ambient light during operation of the device. The means for partitioning off or screening the respective ambient light may be provided in the form of light-impermeable surrounding elements for the control zone. Providing illumination with white light and keeping conditions as constant as possible also enables the detection and evaluation accuracy to be further increased and the color value or color values can be determined with increased reliability. All in all, this also enables the accuracy, reliability and reproducibility of the optical detection of the at least one portion to be improved.

Based on another preferred embodiment of the device, the color-detecting detection device comprises an imaging and/or color-detecting detector, in particular a color camera.

Using an imaging and/or color-detecting detection device further improves detection of the at least one portion of the at least one object. This is especially the case because the detected portion can be resolved by imaging. This represents an improvement compared with detection devices which merely give a mean value for the detected portion based on color values calculated by colorimetry.

Finally, another practical embodiment is one where a test object is disposed on the conveyor means and the color-detecting detection device for optically detecting a portion of the test object incorporating a metal material is disposed in the control zone.

This being the case, the device can be operated in such a way that there is no need to optically detect one of the regular objects treated with treatment fluid. This may be of advantage, for example, if the regular objects are relatively large or bulky items, whereas a corresponding test object can be made relatively small. This means that a control zone used for optically detecting the test object can be of relatively small dimensions. By placing the test object on the conveyor means, it is exposed to the same treatment conditions as the rest of the objects during operation of the device.

In the situation where the objects are containers, only a portion of the corresponding container that is particularly susceptible to discoloration can be simulated by a test object, for example. For example, in the case of a treatment of aluminum containers in the form of cans, the test object might be a closure tab or so-called stay-on tab of the aluminum containers or cans. Such aluminum containers can be treated with treatment fluid in treatment devices, for example for pasteurizing foodstuffs contained in the aluminum containers These closure or opening tabs of aluminum cans have been found to be particularly susceptible to discoloration or water staining during the course of a treatment for pasteurization purposes.

BRIEF DESCRIPTION OF THE DRAWINGS

To provide a clearer understanding, the invention will be described in more detail below with reference to the appended drawings.

These are highly simplified, schematic diagrams illustrating the following.

DETAILED DESCRIPTION OF THE EMBODIMENTS

Firstly, it should be pointed out that the same parts described in the different embodiments are denoted by the same reference numbers and the same component names and the disclosures made throughout the description can be transposed in terms of meaning to same parts bearing the same reference numbers or same component names. Furthermore, the positions chosen for the purposes of the description, such as top, bottom, side, etc., relate to the drawing specifically being described and can be transposed in terms of meaning to a new position when another position is being described.

Figure 1:
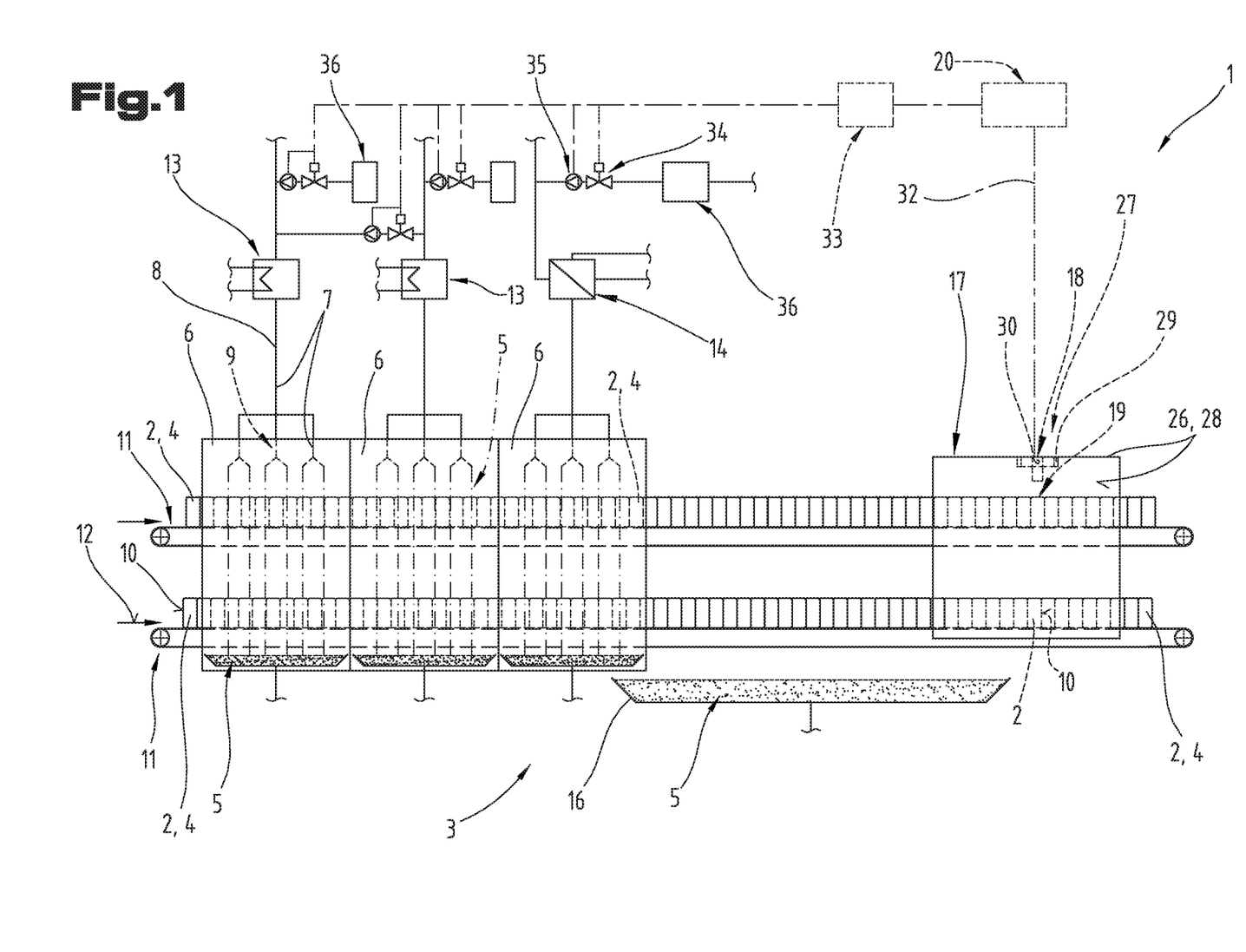
FIG. 1 an example of an embodiment of a device for treating and monitoring objects incorporating a metal material, in a side view.

FIG. 1 is a schematic side view illustrating an example of an embodiment of a device 1 for treating and controlling and/or monitoring the quality of objects 2 incorporating a metal material, in particular an uncoated metal material. The device 1 illustrated as an example of an embodiment is a pasteurizing apparatus 3 or so-called tunnel pasteurizer in which objects 2, in particular in the form of containers 4, can be treated with a treatment fluid 5.

The device 1 and the method will be explained in more detail below on the basis of the examples of embodiments of a pasteurizing apparatus 3 illustrated in the drawings. At this stage, it should be noted that this is only an example of a device 1 and an example of a method and both the device 1 and method might also be different from the specific examples of embodiment of methods and devices for treating metal materials with a treatment fluid. The device 1 and method for treating with treatment fluid and monitoring may also be part of a higher-level method and/or part of a higher-level device. The objects 2 comprising a metal material may be metal containers or closing caps for glass containers or plastic containers, for example screw-caps made of metal material, or the like.

In the case of the pasteurizing apparatus 3 illustrated in FIG. 1 as an example of a device 1, the objects 2 in the form of containers 4 may be filled with contents, in particular a foodstuff, and closed prior to the treatment with treatment fluid, for example. The objects 2 or containers 4 may comprise an aluminum material as the metal material, for example. In particular, the objects 2 or containers 4 treated with treatment fluid 5 in the device 1 or pasteurizing apparatus 3 may be aluminum drink cans, for example, filled with a liquid foodstuff. In such cases, the containers 4 may be closed so as to be liquid-tight or at least as liquid-tight as possible.

For treating the objects 2 or containers 4, the device 1 may comprise a treatment zone 6 or several treatment zones 6. In the example of an embodiment of a pasteurizing apparatus 3 illustrated in FIG. 1, the device 1 comprises three treatment zones 6 for treating the objects 2 with a treatment fluid 5. The three treatment zones 6 each have at least one intake means 7, and in the example of an embodiment illustrated have several intake means 7 for feeding and supplying the treatment fluid 5 into the treatment zones 6. The intake means 7 may be provided in the form of pipelines 8, for example. Furthermore, the intake means 7 may have distributor means 9, such as sprinkler devices or spray nozzles etc., by means of which the treatment fluid 5 can be distributed in the treatment zone(s) 6.

In this manner, during operation of the device 1 or pasteurizing apparatus 3 illustrated as an example in FIG. 1, the method for treating and controlling and/or monitoring, the quality of objects 2 comprising a metal material can be implemented.

The objects 2 or illustrated aluminum containers 4 are treated with a treatment fluid 5 in the treatment zone(s) 6. In the example of an embodiment of the device 1 illustrated in FIG. 1, the latter are so-called tunnel pasteurizers, and the treatment fluid 5 is applied to and acts on a respective external face 10 of the objects 2 or containers 4 in the treatment zones 6.

The treatment fluid 5 for treating the objects 2 can be reused, in other words can be used repeatedly for treating the objects 2 in the treatment zone(s) 6. To this end, the treatment fluid 5 is circulated in a circuit (not illustrated) for example, and is repeatedly delivered to the treatment zone(s) 6.

In particular, the objects 2 or containers 4 comprising a metal material are treated with an aqueous treatment fluid 5. Generally speaking, treatments with an aqueous treatment fluid 5 may have advantages from several points of view. For example, cleaning or surface or tempering treatments of objects 2 incorporating a metal material can be effectively operated using an aqueous treatment fluid 5. This is especially the case because the properties of aqueous fluids can be readily and very effectively adjusted by adding chemicals. By using an aqueous treatment fluid 5 with an appropriate chemical composition, a respective metal material of the objects 2 can be treated in a specific way. Furthermore, aqueous treatment fluids 5 can be tempered in a relatively broad temperature range and aqueous treatment fluids are generally readily available.

The objects 2 or containers 4 to be treated are preferably conveyed to the device 1 by a conveyor means 11 which is used to convey the objects 2 through the treatment zone 6 or through several consecutive treatment zones 6. Such a conveyor means 11 might be a conveyor belt, for example, on which the objects 2 can be placed or positioned. In the case of the pasteurizing apparatus 3 illustrated in FIG. 1 as an example of a device 1, two such conveyor means 11 are provided so that the objects 2 or containers 4 filled with foodstuff can be conveyed through the consecutive treatment zones 6 in two conveyor planes one above the other in a transport direction 12 during operation of the device 1.

In order to treat the objects 2 or containers 4 in the treatment zone(s) 6, a respective external face 10 can be treated with a tempered treatment fluid 5 in the treatment zones 6. To this end, the device 1 may comprise a heating mechanism 13 for heating the treatment fluid 5 and a cooling mechanism 14 for cooling the treatment fluid 5. By these devices 13, 14 for tempering the treatment fluid 5 and/or also by mixing treatment fluids at different temperatures, a respective treatment zone 6 can be supplied with treatment fluid 5 at a specifically set temperature.

Heating mechanism 13 and cooling mechanism 14 are only schematically indicated in each case in FIG. 1. Naturally, depending on the system or apparatus, one or more heating mechanism 13 and cooling mechanism 14 may be provided. For example, heat exchangers may be provided, through which heating or cooling medium is circulated, by means of which the treatment fluid 5 can be heated or cooled to a specific degree. Such heat exchangers may in turn be supplied by heating and/or cooling devices. For example, steam heaters or cooling towers or heat pumps may be used for this purpose.

In the case of the example of an embodiment of a pasteurizing apparatus 3 or tunnel pasteurizer illustrated in FIG. 1, at least a first treatment zone 6 may be used as a way of heating the objects 2 or containers 4, for example the left-hand treatment zone 6 illustrated in in FIG. 1. This treatment zone may be supplied with a heated treatment fluid 5 for heating or pre-heating the objects 2 or containers 4. Furthermore, relative to the transport direction 12 of the objects 2, at least a second treatment zone 6 for additionally heating the objects 2 or containers filled with foodstuff 4 may be disposed after the first treatment zone 6. Furthermore, relative to the transport direction 12 of the objects 2, at least a third treatment zone 6 for cooling the objects 2 or containers 4 may be disposed after the second treatment zone 6. It would naturally also be possible to provide more than one treatment zone 6 respectively for heating, further heating and cooling.

The treatment, zones 6 illustrated in FIG. 1 may be supplied with an appropriately tempered treatment fluid 5 for the purpose of heating, further heating and finally cooling the objects 2 respectively. For example, the objects 2 can be treated in at least one treatment zone 6 with a treatment fluid 5 having a temperature of between 45° C. and 130° C., In particular in the case of the pasteurizing apparatus 3 illustrated as an example in FIG. 1, the objects 2 or filled and closed containers 4, can be treated in at least one treatment zone 6, in particular in treatment zone 6 illustrated in the middle in FIG. 1, with a treatment fluid 5 having a temperature of between 50° C. and 100° C., preferably having a temperature of between 60° C. and 90° C., Based on this operating mode, the foodstuff in the closed containers 4 can be pasteurized in the at least one treatment zone 6.

As also illustrated in FIG. 1, the device 1 may be provided with another treatment zone 15 for removing or drying the treatment fluid 5 on the objects 2. This other treatment zone 15 for removing the treatment fluid 5 from the objects 2 or containers 4 may be disposed after the treatment zone(s) 6 for treating with treatment fluid 5 in the transport direction 12 of the objects 2. The objects 2 having been treated with treatment fluid 5, the treatment fluid 5 is removed from the treated objects 2 or dried in this other treatment zone 15.

This being the case, the treatment fluid 5 may be drained and/or evaporated off the objects 2 or containers 4 in the other treatment zone 15, for example. This may be done passively and without additional aids. The drained and draining treatment fluid 4 may be collected in a collection container 16 for example, and fed away from the device 1 or reused. As an alternative to the example of an embodiment, illustrated in FIG. 1, removal or drying may be done actively, i.e. assisted by appropriate means. Such drying methods and the configuration of such other treatment zones 6 for removing and/or drying the treatment fluid 5 on objects 2 will be explained in more detail below with reference to other examples of embodiments.

The essential thing for the device 1 is that a control zone 17 is provided, as also illustrated in FIG. 1. Disposed in this control zone 17 for constantly monitoring the objects 2 treated with treatment fluid 5 is a color-detecting or color-measuring detection device 18 for optically detecting at least one portion 19 of at least one object 2 incorporating an uncoated metal material treated with treatment fluid 5. As may also be seen from FIG. 1, the color-detecting detection device 18 is connected to an evaluation device 20 by signal transmission to enable the optically detected data relating to the at least one portion 19 to be processed. This being the case, the evaluation device 20 is configured to colorimetrically evaluate the supplied data by determining a color value or several color values.

During operation of the device 1 or the illustrated pasteurizing apparatus 3, at least one portion 19 comprising a metal material respectively of at least one object 2 treated with treatment fluid 5 is optically detected by means of the color-detecting or color-measuring detection device 18, thereby providing constant monitoring, after treating the objects 2 in this manner. The optically detected data of the at least one portion 19 is calorimetrically evaluated by means of an evaluation device 19 by determining a color value or several color values. This colorimetric evaluation may be implemented on the basis of a color model for example, whereby numerical characteristic values are defined in order to characterize or define a color.

Defects caused by the treatment can therefore be picked up by detecting and colorimetrically evaluating discoloration of metal materials constantly during the operation of treating the objects 2 with treatment fluid 5. This in turn enables the efficiency of the treatment with treatment fluid 5 to be improved because if discoloration is detected based on the colorimetric evaluation, counter-actions can be initiated in order to prevent defective treatment.

The color-detecting detection device 18 may in principle be any type of detection device by means of which light and/or colors can be reliably detected, for example by color measuring devices operating on the basis of spectral resolution and/or spectral photometry. In principle, the detection device 18 may comprise a plurality of detection means, for example color sensors or color measuring devices for detecting several portions 19 or even all of the portions respectively of the at least one object 2 or container 4 treated with treatment fluid 5. In most cases, however, optical detection can be limited to one portion 19 of an object 2. In particular, this may be a portion 19 where a change due to treatment with a treatment fluid 5 is particularly likely. In the case of the pasteurizing apparatus 3 illustrated as an example of an embodiment of a device 1 in FIG. 1, an upper or upwardly directed portion 19 of the objects 2 or containers 4, for example, is monitored by optical detection and colorimetric evaluation, as illustrated.

In the example of a device 1 for treating objects 2 incorporating a metal material, illustrated in the form of a pasteurizing apparatus 3, aluminum containers 4 or aluminum cans filled with a foodstuff, in particular a drink, may be the objects 2 incorporating an aluminum material that are treated with aqueous treatment fluid 5 and then monitored, for example. In this instance, it may be of advantage for at least one portion 19 incorporating aluminum material respectively of the at least one object 2 to be optically detected. In this manner, discoloration such as often occurs during a treatment of objects incorporating aluminum material 2 with aqueous treatment fluid 5, namely so-called wet storage stain or water staining, can be optically detected and colorimetrically evaluated. Such aluminum containers 4 usually have a closure or opening tab in the form of a so-called stay-on tab in an upper portion 19 or on the top face. Experience has shown that this portion 19 is particularly susceptible to discoloration and can undergo color changes particularly rapidly during a treatment with aqueous treatment fluid 5. In particular, discoloration or water staining can occur first and foremost in this portion 19 during the course of treating such aluminum containers 4 with treatment fluid, which is why it is particularly meaningful to optically detect and colorimetrically evaluate this portion 19 to enable discoloration of the corresponding objects 2 to be detected rapidly and reliably.

As may also be seen from FIG. 1, the at least one portion 19 respectively of the at least one object 2 or the at least one container 4 treated with treatment fluid 5 can be optically detected after being conveyed through the last consecutive treatment zone 6 in the transport direction 12. To this end, the control zone 17 for the objects 2 or containers 4 may be disposed after the last treatment zone 6, 15 relative to the transport direction 12. The at least one object 2 to be optically detected may be conveyed respectively through the control zone 17 comprising the color-detecting detection device 18. To this end, the conveyor 11 can be configured to convey the at least one object 2 respectively through the control zone 17, for example.

Figure 2:
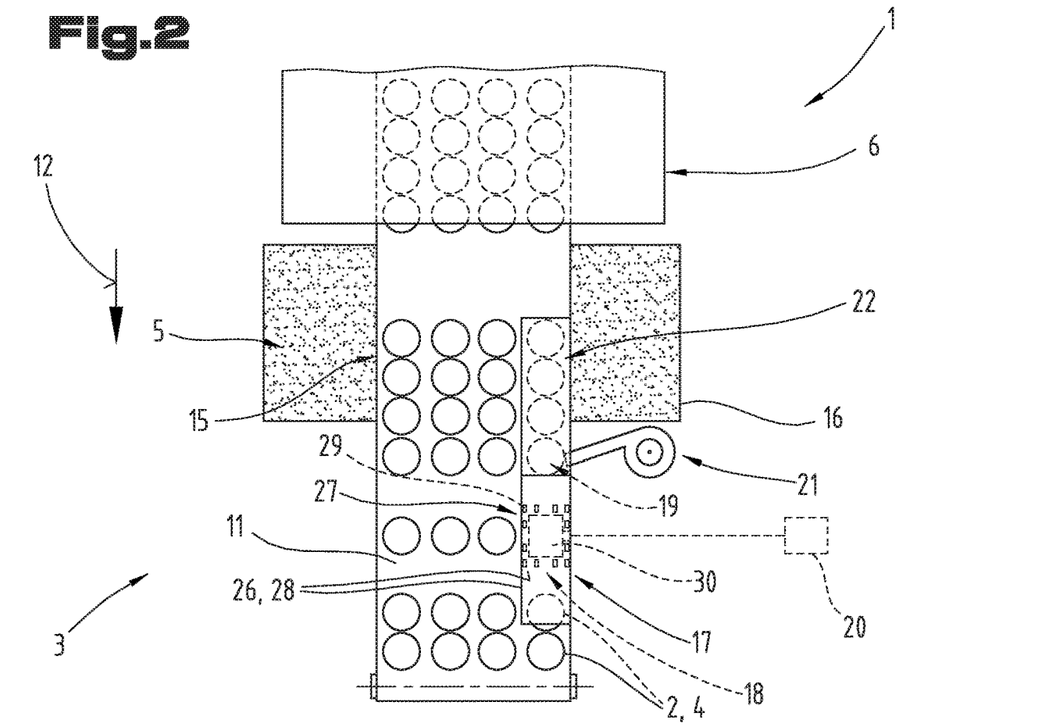
FIG. 2 parts of an example of an embodiment of a device for treating and monitoring objects incorporating a metal material, in a plan view.

Generally speaking, there are several possible ways of implementing quality control and/or monitoring of the objects 2 incorporating a metal material after their treatment with treatment fluid 5. One possible option is illustrated in FIG. 2 and FIG. 2 illustrates parts of an example of an embodiment of a device 1 for treating and controlling and/or monitoring the quality of objects 2 incorporating a metal material. To provide better clarity, the device 1 is shown in a plan view. The same reference numbers and component names are used in FIG. 2 to denote parts that are the same as those described above in connection with FIG. 1. To avoid unnecessary repetition, reference may be made to the more detailed description of FIG. 1 given above. In FIG. 2 and also in all the subsequent drawings, only a few of the objects 2 or containers 4 are illustrated in order to retain better clarity. In reality, of course, the objects 2 are packed into the device 1 as densely as possible and treated with treatment fluid 5.

As may be seen from FIG. 2, the color-detecting detection device 18 can be disposed and/or oriented in the control zone 17 in such a way that at least a part quantity can be constantly or continuously monitored, or at least one of the treated objects 2 or containers 4 can be constantly monitored by optically detecting the at least one portion 19. In the embodiment illustrated as an example, at least one portion 19 of at least one object 2 or container 4 disposed in a side row on the conveyor 11 in the transport direction 12 is optically detected, for example. Naturally, the color-detecting detection device 18 could also be configured to optically detect at least one object 2 in a centrally disposed row of objects 2 treated with treatment fluid 5 on the conveyor 11 by reference to the transport direction 12. As an alternative to the example of an embodiment illustrated in FIG. 2, it would also be possible to separate out a part quantity of treated objects 2 in order to optically detect the at least one portion 19. This may be done, for example, by diverting a part quantity of treated objects 2 by means of a deflection device, which might be a baffle element, for example a baffle plate, and then feeding them through a control zone 17.

In principle, it is also possible to optically detect at least one treated object 2 respectively of several rows of objects 2 disposed in the transport direction 12. It would naturally also be conceivable for all of the objects 2 treated with treatment fluid 5 to be optically detected by means of the color-detecting detection device 18.

Figure 3:
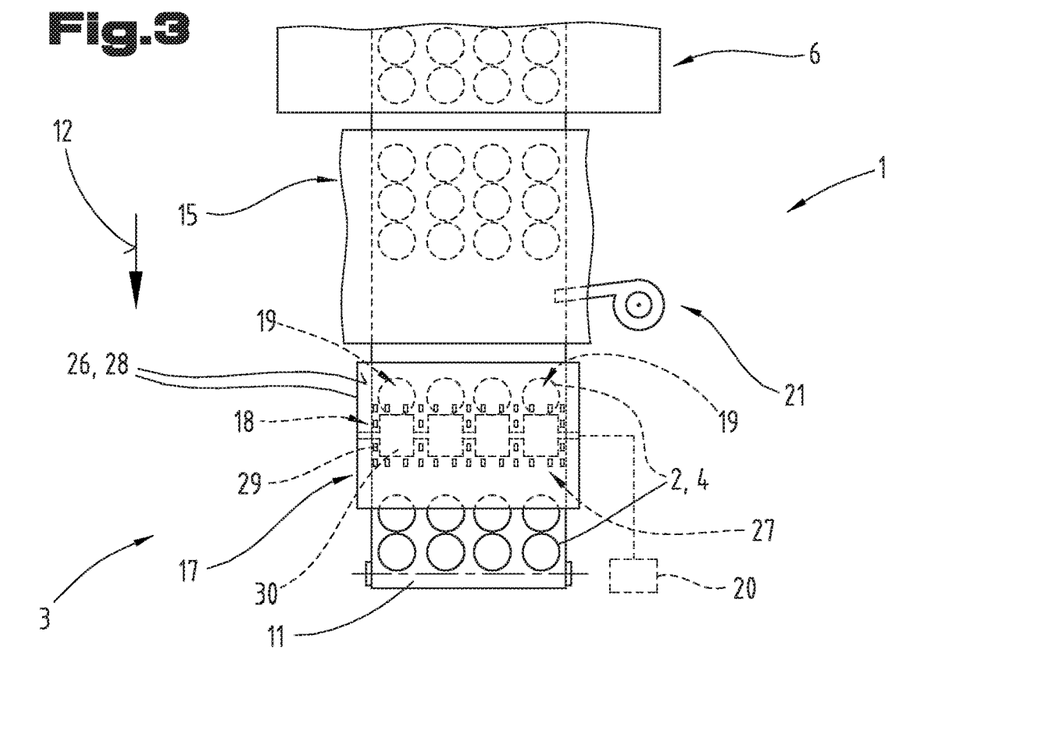
FIG. 3 parts of another example of an embodiment of a device for treating and monitoring objects incorporating a metal material, in a plan view.

To this end, the color-detecting detection device 18 may comprise a detector with a detection range of large dimensions for example, or alternatively several detectors, as indicated in FIG. 3. In FIG. 3 again, the same reference numbers and component names are used to denote parts that are the same as those described in connection with FIG. 1 and FIG. 2 above. To avoid unnecessary repetition, reference may be made to the more detailed description of FIG. 1 and FIG. 2 given above.

Generally speaking, the detection device 18 can be positioned at various points in the control zone 17 to enable different portions 19 incorporating a metal material to be detected respectively.

In principle, both in the case of the example of an embodiment illustrated in FIG. 2 and that in FIG. 3, as well as quite generally, the color-detecting detection device 18 can be configured to optically detect at least one of the objects 2 or containers 4 treated with treatment fluid 5 respectively at set time intervals. Optical detection may also be run after treating a specific, set number of objects 2 with treatment fluid 5, for example.

Alternatively, it would naturally also be possible for at least a part quantity of the treated objects 2 to be optically detected on a continuous basis. In particular, in the case of the embodiment illustrated as an example in FIG. 2 or FIG. 3, a detection frequency of the respective color-detecting detection device 18 can be coupled with timing of the conveying frequency of the objects 2 or containers 4 through the control zone 17. In this connection, it would also be possible for the frequency of the colorimetric evaluation to be coupled with the detection frequency.

Furthermore, an illuminating brightness of the illuminating device 27 for the at least one portion 19 to be optically detected can be adapted to a speed at which the object 2 to be optically detected is conveyed through the control zone 17. This primarily enables a sufficient illuminating brightness to be obtained respectively for different illumination times for the at least one portion 19 to be optically detected respectively, depending on the conveying speed. In this respect, a conveying speed may also depend on the frequency at which the object 2 to be optically detected is conveyed through the control zone 17.

In the case of the embodiment illustrated as an example in FIG. 3, another treatment zone 15 is provided for removing and/or drying the treatment fluid 5 from the objects 2 treated with treatment fluid 5. As an alternative to the embodiment of another treatment zone 15 illustrated as an example in FIG. 1, residues of treatment fluid can also be actively removed from the treated objects 2 or containers 4, as illustrated in FIG. 3. To this end, the other treatment zone 15 illustrated in FIG. 3 can be provided with hot air fans 21, for example, by means of which an active or assisted removal of the treatment fluid 5 from the treated objects 2 can be implemented.

With a view to preventing the optical detection of the at least one portion 19 and the colorimetric evaluation of the detected portion 19 from being affected by treatment fluid 5 or treatment fluid residues, an additional zone 22 may also be provided for actively removing treatment fluid 5 from the objects 2 to be optically detected as rapidly and completely as possible, as illustrated in FIG. 2 for example. In the embodiment illustrated as an example in FIG. 2, an additional zone 22 for removing treatment fluid 5 from the at least one object 2 presented for optical detection is disposed after the last treatment zone 6 for treating the objects 2 with treatment fluid 5 relative to the transport direction 12 of the objects 2 This additional zone 22 may in turn be provided with a hot air fan 21, for example, or some other drying means. In the embodiment illustrated as an example in FIG. 2, such an additional zone 22 is disposed in this instance parallel with the other treatment zone 15 for passively removing treatment fluid 5 from objects 2 or containers 4 that will not be presented for optical detection. In the additional zone 22 for active removal, the treatment fluid 5 on the at least one object 2 respectively that will be presented for optical detection can be removed and treatment fluid 5 can be removed as completely and rapidly as possible. Relatively speaking, this is faster than the passive drying of objects 2 treated with treatment fluid 5 that takes place in the other treatment zone 15.

Figure 4:
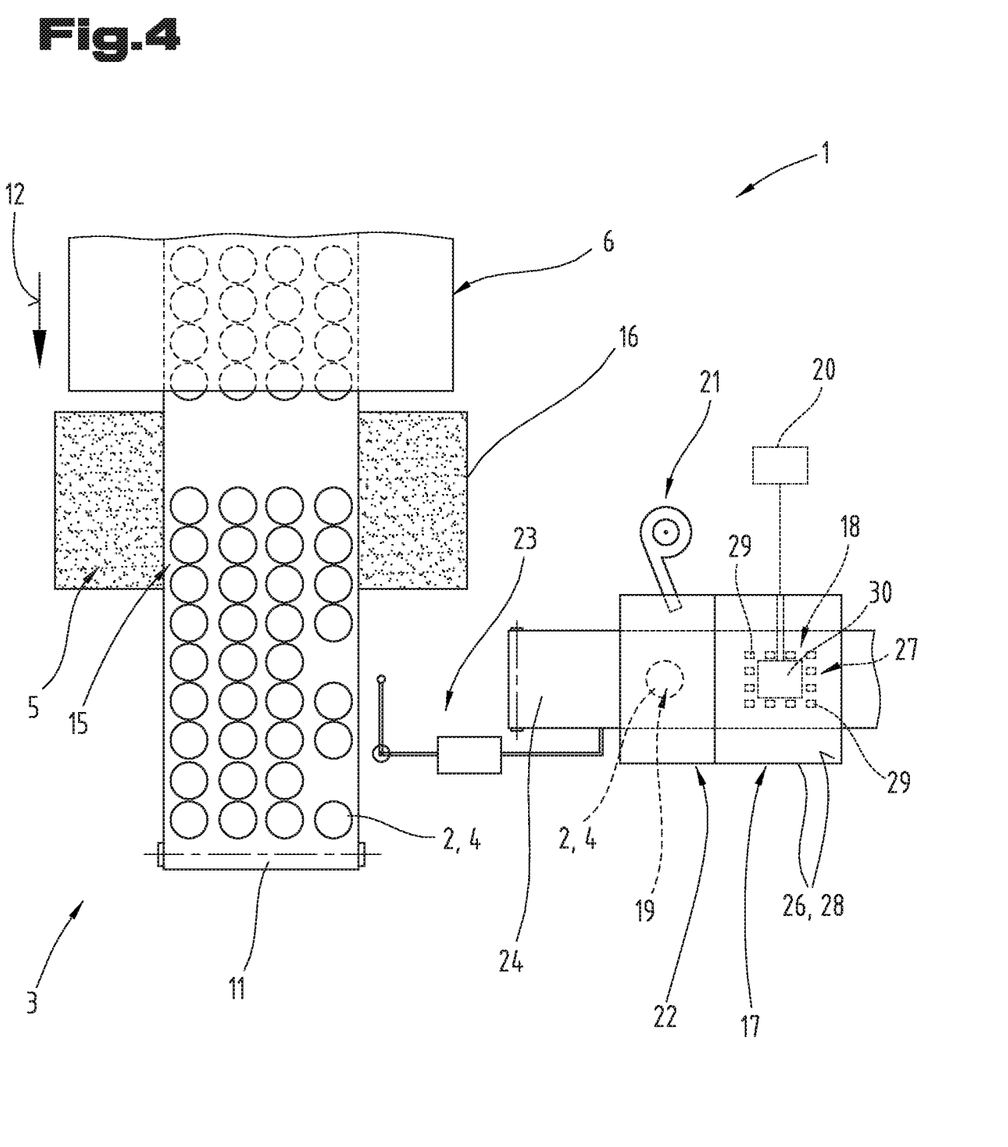
FIG. 4 parts of another example of an embodiment of a device for treating and monitoring objects incorporating a metal material, in a plan view.

FIG. 4 illustrates another and optionally independent embodiment of the device for treating objects incorporating a metal material with treatment fluid, the same reference numbers and component names being used to denote parts that are the same as those described above in connection with FIG. 1 to FIG. 3. To avoid unnecessary repetition, reference may be made to the more detailed description, of FIG. 1 to FIG. 3 given above.

In principle, as illustrated in FIG. 4, detection may also be operated on a random basis. For example, at specific points in time, an object 2 or container 4 treated with treatment fluid 5 may be taken from the conveyor means 11 for optically detecting the at least one portion 19 incorporating a metal material and conveyed to a separately disposed control zone 17, as illustrated in FIG. 4. A random sample can be manually picked, i.e. by an operator by hand for example, in which case an object 2 to be optically detected can be picked up from the conveyor means 11, dried by wiping it and then taken to a control zone. As illustrated in FIG. 4, this removal process may naturally also be mechanically operated, in particular on an automated basis, for example by means of a removal mechanism 23. Such a removal mechanism 23 might be a mechanical gripper, a suction cup type of gripping element operated at vacuum pressure or any other gripping device for gripping or removing the at least one object 2 or container 4 respectively to be presented for optical detection. Alternatively, individual treated objects 2 to be presented for optically detecting the at least one portion 19 may also be removed by means of a pivotable deflector device, for example by means of a deflector element or baffle plate, after which the separated or deflected objects 2 are conveyed through the control zone 17.

In the case of the embodiment illustrated as an example in FIG. 4, another conveyor device 24 is provided for conveying the at least one object 2 to be presented for optical detection through the separately disposed control zone 17. Furthermore, in the case of the device 1 or pasteurizing apparatus 3 exemplarily and partially illustrated here, the other conveyor device 24 also conveys an object 2 to be presented for optical detection respectively through an additional zone 22 for removing the treatment fluid 5 and/or removing treatment fluid residues from the at least one object 2 to be presented for optical detection respectively before it is conveyed through the control zone 17.

Figure 5:
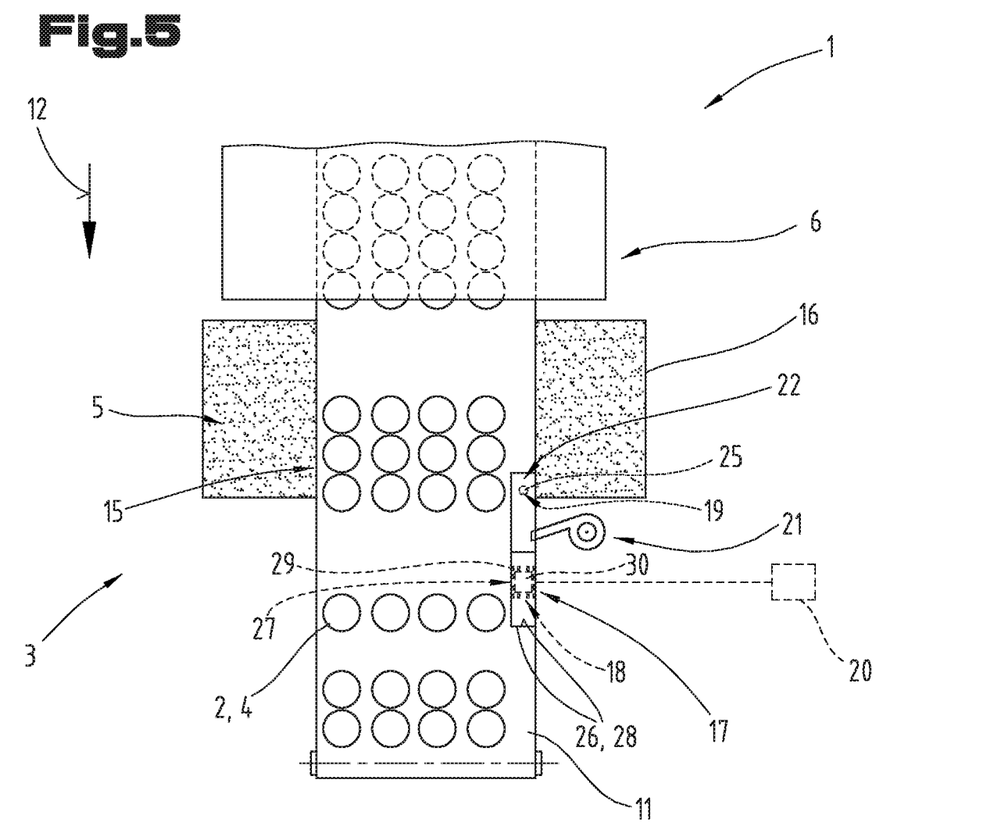
FIG. 5 parts of another example of an embodiment of a device for treating and monitoring objects incorporating a metal material, in a plan view.

FIG. 5 illustrates another and optionally independent embodiment of the device for treating objects incorporating a metal material with treatment fluid, the same reference numbers and component names being used to describe parts that are the same as those described in connection with FIG. 1 to FIG. 4 above. To avoid unnecessary repetition, reference may be made to the more detailed description of FIG. 1 to FIG. 4 given above.

FIG. 5 illustrates an example of an embodiment of a device 1 in which a test object 25 is disposed on the conveyor 11 and the color-detecting detection device 18 is disposed in the control zone 17 for optically detecting at least one portion 19 of this test object 25 incorporating a metal material. To save on space, such a test object 25 may be disposed in a peripheral region of the conveyor 11, for example. Furthermore, such a test object 25 may be of small dimensions compared with the other treated objects 2. This in turn offers advantages in terms of the dimensions necessary for the control zone 17, which can likewise be designed with relatively small dimensions in this case.

Based on the example of an embodiment illustrated in FIG. 5, the test object 25 is treated with treatment fluid together with the objects 2 to be treated. To this end, the test object 25 can be conveyed through the treatment zone(s) 6 together with the objects 2 to be treated. After being treated with treatment fluid 5, a portion 19 of the test object 25 incorporating metal material can be optically detected by means of the color-detecting detection device 18.

Such a test object 25 might be used, to imitate or model a portion of the objects 2 to be treated that is particularly susceptible to discoloration, for example. For example, if can-type aluminum containers 4 are to be treated in the pasteurizing apparatus 3 illustrated as an example of a treatment device 1, the test object 25 may be provided in the form of a closure or so-called stay-on tab of the aluminum containers 4. These closure and/or opening tabs of aluminum containers 4 have proved to be particularly susceptible to discoloration or water staining during the course of a treatment for pasteurization purposes.

As also illustrated in FIGS. 1 to 5, it may be preferable to provide a respective control zone 17 with means 26 for partitioning off and/or screening off ambient light and an illuminating device 27, in particular an LED-illuminating device, for illuminating the at least one portion 19 of the at least one object 2 respectively with white light, in this manner, a detection area of the color-detecting detection device 18 in a control zone 17 can be at least largely closed or screened off from the prevailing ambient light and the at least one portion 19 of the at least one object 2 to be optically detected by means of the illuminating device 27 respectively, in particular LED-illuminating device, can be illuminated with white light.

As a result of these features or actions, the optical detection conditions for the at least one portion 19 incorporating a metal material of the at least one object 2 to be presented for optical detection can be made as uniform and reproducible as possible. The means 26 for partitioning or screening off the respective ambient light may be provided in the form of light-impermeable wall-type surrounding or screening elements 28 for the control zone 17, for example, thereby providing a control zone 17 surrounded by a tunnel-type or roof-type screening element, as illustrated in FIG. 1 to FIG. 4.

The white light-illuminating device 27 may comprise one or more light sources 29, preferably LED-light sources. The number and disposition of LED-light sources 29 in the control zone 17 may be freely selected in such a way that the at least one portion 19 of the at least one object 2 or container 4 respectively presented for detection is lit or illuminated sufficiently and as uniformly as possible with white light.

As may also be seen from FIG. 1 to FIG. 5, the color-detecting detection device 18 may comprise an imaging and/or color imaging detector 30, in particular a color camera. Accordingly, the at least one portion 19 of the at least one object to be detected 2 respectively to be optically detected can be detected and/or imaged by means of an imaging detector 30, in particular a color camera during operation of the device 1.

Figure 6:
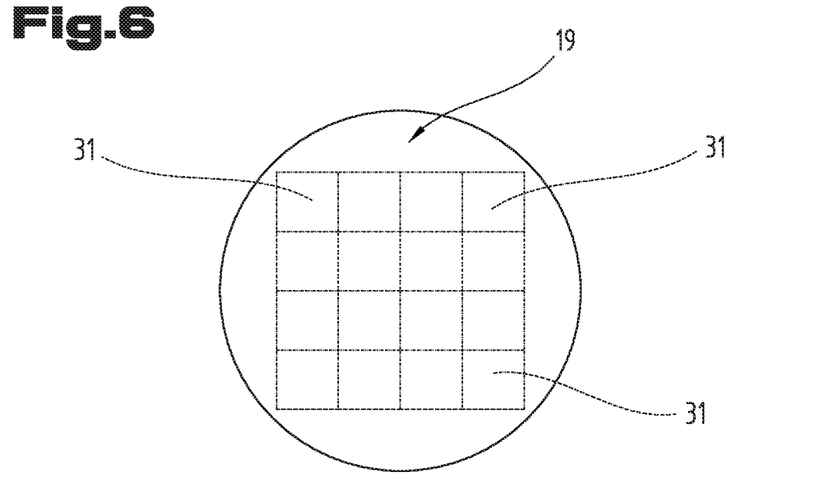
FIG. 6 a plan view of an optically detected portion of a treated object.

Detecting a color image in particular enables the options for the calorimetric evaluation by the evaluation device 20 to be increased. In this connection, it may be for example that the optically detected image of the at least one portion 19 is broken down into part-images 31 and every part-image 31 is colorimetrically evaluated separately, as schematically illustrated in FIG. 6. In this manner, discoloration in the at least one detected portion 19 can be analyzed on the basis of areas or part-images using resolution. This enables points or areas exhibiting maximum discoloration to be identified, for example.

In principle, the evaluation device 20 may be disposed structurally separately from the detection device 18, as also schematically illustrated in FIGS. 1 to 5 respectively. Any type of data transmission means may be used to transmit the optically detected data to the evaluation device 20 in principle. A hard-wired or wireless signal connection 32 may be provided between the color-detecting detection device 18 and the evaluation device 20, as illustrated in FIG. 1 to FIG. 5. The evaluation device 20 itself may be provided in the form of a software controllable computer unit for example, such as a PC or a tablet. In principle, however, the evaluation device 20 may be an integral component of the detection device 18, for example color sensors with an integrated evaluation device 20 based on a color model.

The colorimetric evaluation by means of the evaluation device 20 may preferably be implemented in such a way that the at least one optically detected portion 19 of the at least one object 2 is respectively evaluated in the L*a*b* color space and the L* color value and/or a* color value and/or b* color value is calorimetrically determined on the basis of an evaluation.

The L*a*b* color space constitutes a color model for calorimetric evaluation which is independent of any device and which is defined as close as possible to human perception. Accordingly, any discoloration of metal materials can also be evaluated as effectively as possible in terms of human perception of discoloration.

Based on the pasteurizing apparatus 3 illustrated as an example of a device 1 in FIG. 1 to FIG. 5 designed for containers 4 incorporating an aluminum material and objects 2 filled with foodstuff, the objects can be treated with tempered aqueous treatment fluid 5 for pasteurization purposes. With such treatments and/or processes involving objects 2 incorporating aluminum using aqueous treatment fluid 5, so-called water staining of the aluminum material often occurs for example. However, this discoloration of aluminum materials known as wet storage stain is often difficult to detect and/or evaluate. In such cases, the b* color value can be numerically generated or determined on the basis of colorimetry. The b* color value is particularly well suited to colorimetric evaluation of wet storage stain. In particular, it has been found that brownish to black discoloration due to water staining can be evaluated particularly well using colorimetry to determine the b* color value. In particular in the event of wet storage stain, a significant increase in the b* color value towards higher, positive values can be ascertained or observed compared with an untreated aluminum material or a clean aluminum surface. Alternatively and/or in addition, if optically detected wet storage staining occurs in the at least one optically detected portion 19, a colorimetric evaluation may also be implemented by determining the L* color value, which defines the brightness or luminance of a respective color.

Independently of an exactly implemented colorimetric evaluation, a threshold value may be set respectively for the colorimetrically determined color value(s) and the color value(s) can be compared with the correlated threshold value. In principle, a correlated threshold value can be set respectively for every color value determined by colorimetry and/or evaluation. By comparing a color value with the respectively associated threshold value, the extent of discoloration can then be efficiently determined and assessed and/or numerically analyzed by computer.

In principle, during the course of the colorimetric evaluation, color values can be examined and evaluated by a person, for example by an operator of the device 1, and/or compared with a respective threshold value for example. With a view to obtaining efficient automation of treatment processes, however, it may be of advantage if these processes are automated using control technology, in other words a comparison of a colorimetrically determined color value with a set and/or stored threshold value for the corresponding color value.

A threshold value and/or threshold values for color values can be and/or are stored in the evaluation device 20 itself, for example using a data processing system. However, the evaluation device 20 may also be connected to a control device 33 by signal transmission, as schematically illustrated in FIG. 1. Threshold value(s) can then also be stored in the control device 33 using a data processing system.

In this connection, however, it may also be that if a set threshold value is exceeded by a color value correlated with this threshold value, an action is implemented or several actions are implemented. For example, it may be expedient if the action is to trigger an alarm. In principle and depending on a respective treatment process, implementation of the method may also be halted for example, by halting the conveyor 11 and/or stopping the intake of treatment fluid to the treatment zone(s), for example. An action can also be initiated manually by an operator of the device.

However, it may also be preferable to initiate an action, for example an alarm or stopping the treatment, on an automated basis and/or using control technology, for example by means of a control device 33, as illustrated in FIG. 1.

In the example of an embodiment of a device 1 illustrated in FIG. 1 on the basis of a pasteurizing apparatus 3, the action might be to make a change to the chemical composition of the treatment fluid 5, for example. In particular, also with a view to preventing water staining of an object 2 or container 4 incorporating aluminum material, the pH value of the aqueous treatment fluid 5 may be adjusted and/or inhibitors added to the treatment fluid 5, in particular phosphonates, and/or water hardness regulators may be added to the treatment fluid 5.

As illustrated in FIG. 1, in order to implement such actions on an automated basis using control technology, the control device 33 may be connected to appropriate co-operating means, such as for example the valves 34 and/or pumps 35 schematically illustrated in FIG. 1 which can be activated by the control system by signal transmission. In this manner, the valves 34 can be opened by the control system and/or the pumps 35 activated by the control system in order to meter and deliver appropriate chemicals to the treatment fluid, for example from chemical tanks 36. Accordingly, the chemical tanks 36 illustrated in FIG. 1 may contain acids and/or bases and/or inhibitors and/or hardness regulators and/or other chemicals, for example.

If the treatment fluid 5 is used repeatedly for treating the objects 2, one action might be to partially or totally replace the treatment fluid 5, in other words at least partially replace it with fresh treatment fluid 5. This action is of particular advantage in the case of methods whereby the treatment fluid 5 of the treatment zone(s) 6 is repeatedly circulated through a circuit.

Alternatively or in addition, however, the action might be to change a conveying speed of the objects 2 through the treatment zone(s) or to halt conveying. Finally, in order to prevent discoloration caused by the treatment of objects incorporating a metal material with a treatment fluid, it may also be expedient if the action is to change an intake temperature of a treatment fluid 5 fed into a treatment zone 6.

The embodiments illustrated as examples represent possible variants and it should be pointed out at this stage that the invention is not specifically limited to the variants specifically illustrated, and instead the individual variants may be used in different combinations with one another and these possible variations lie within the reach of the person skilled in this technical field given the disclosed technical teaching.

The protective scope is defined by the claims. However, reference may be made to the description and drawings with a view to interpreting the claims. Individual features or combinations of features from the different examples of embodiments described and illustrated may also be construed as independent embodiments of the solutions proposed by the invention. The objective underlying the individual solutions proposed by the invention may be found in the description.

All the figures relating to ranges of values in the description should be construed as meaning that they include any and all part-ranges, in which case, for example, the range of 1 to 10 should be understood as including all part-ranges starting from the lower limit of 1 to the upper limit of 10, i.e. all part-ranges starting with a lower limit of 1 or more and ending with an upper limit of 10 or less, e.g. 1 to 1.7, or 3.2 to 8.1 or 5.5 to 10.

For the sake of good order, finally, it should be pointed out that, in order to provide a clearer understanding of the structure, elements are illustrated to a certain extent out of scale and/or on an enlarged scale and/or on a reduced scale.

| List of reference numbers | |
|---|---|
| 1 | Device |
| 2 | Object |
| 3 | Pasteurizing apparatus |
| 4 | Container |
| 5 | Treatment fluid |
| 6 | Treatment zone |
| 7 | Intake means |
| 8 | Pipeline |
| 9 | Distributor means |
| 10 | External face |
| 11 | Conveyor means |
| 12 | Transport direction |
| 13 | Heating means |
| 14 | Cooling means |
| 15 | Treatment zone |
| 16 | Collection container |
| 17 | Control zone |
| 18 | Detection device |
| 19 | Portion |
| 20 | Evaluation device |
| 21 | Hot air fan |
| 22 | Zone |
| 23 | Removal mechanism |
| 24 | Conveyor device |
| 25 | Test object |
| 26 | Means |
| 27 | Illuminating device |
| 28 | Screening element |
| 29 | Light source |
| 30 | Detection means |
| 31 | Part-image |
| 32 | Signal connection |
| 33 | Control device |
| 34 | Valve |
| 35 | Pump |
| 36 | Chemical tank |

The invention claimed is:

1. A method for treating and monitoring objects comprising containers formed of a metal material, the method comprising the following steps:
   filling the objects with foodstuff and closing the objects;
   treating the filled objects with a treatment fluid in a treatment zone or in several treatment zones, wherein a respective external face of each of the objects is treated with a tempered treatment fluid in at least one of the treatment zones and wherein the foodstuff is pasteurized in the at least one treatment zone during the step of treating;
   thereafter removing or drying the treatment fluid from the objects treated,
   optically detecting by means of a color-detecting detection device at least one portion comprising metal material of at least one of said treated objects to provide constant monitoring after treating the objects, wherein the step of optically detecting is performed after the step of treating, and
   colorimetrically evaluating the optically detected data of the at least one portion with an evaluation device by determining a color value of a color space or several color values of a color space.

2. The method according to claim 1, wherein the objects are conveyed by means of a conveyor in a transport direction through one or more consecutive treatment zones, and after being conveyed through a last one of the consecutive treatment zones in the transport direction, the at least one portion of the at least one object is optically detected.

3. The method according to claim 1, wherein the at least one object is conveyed through a control zone comprising the color-detecting detection device.

4. The method according to claim 1, wherein the objects comprise an aluminum material and are treated with aqueous treatment fluid, and wherein at least one portion comprising aluminum material of the at least one object is optically detected.

5. The method according to claim 1, wherein the objects are treated with a treatment fluid having a temperature of between 45° C. and 130° C. in at least one treatment zone.

6. The method according to claim 1, wherein the treatment fluid is removed from the at least one object prior to optical detection of the at least one portion.

7. The method according to claim 1, wherein a detection area of the color-detecting detection device is screened off with a screening element, and the at least one portion of the at least one object to be optically detected is illuminated with white light by an illuminating device.

8. The method according to claim 7, wherein a light intensity of the illuminating device for the at least one portion to be optically detected is adapted to a conveying speed of the object to be optically detected through the control zone.

9. The method according to claim 1, wherein a threshold value is set for the colorimetrically determined color value(s) and the color value(s) is/are compared with the associated threshold value.

10. The method according to claim 9, wherein when a set threshold value is exceeded by a color value associated with this threshold value, an action is implemented or several actions are implemented.

11. The method according to claim 10, wherein the action comprises triggering an alarm.

12. The method according to claim 10 wherein the action comprise a change to the chemical composition of the treatment fluid.

13. The method according to claim 12, wherein the action comprises adjusting the pH value of the treatment fluid or adding inhibitors to the treatment fluid or adding water hardness regulators to the treatment fluid.

14. The method according to claim 10, wherein the action comprises varying a conveying speed of the objects through treatment zone(s) or halting conveying.

15. The method according to claim 10, wherein the action comprises varying an intake temperature of a treatment fluid fed into a treatment zone.

16. The method according to claim 1, wherein the at least one optically detected portion of the at least one object is colorimetrically evaluated in the L*a*b* color space, and the L* color value and/or a* color value and/or b* color value is colorimetrically determined.

17. The method according to claim 1, wherein the at least one portion of the at least one object is optically detected by an imaging detection device.

18. The method according to claim 17, wherein the optically detected image of the at least one portion is broken down into part-images comprising regions or image positions, and each part-image is colorimetrically evaluated separately.

19. The method according to claim 1, wherein a test object is treated with treatment fluid together with the objects to be treated, and a portion of the test object comprises a metal material and is optically detected by the color-detecting detection device after the treatment.

20. The method according to claim 19, wherein the test object is conveyed through treatment zone(s) together with the objects to be treated.

* * * * *